US004001563B2

United States Statutory Invention Registration [19]

[11] Reg. Number: H1563

[45] Published: Jul. 2, 1996

Snyder et al.

[54] CHEMICAL AGENT MONITOR FOR IMMUNOASSAY DETECTION

[75] Inventors: A. Peter Snyder; Maryalice Miller, both of Bel Air, Md.; David A. Blyth, Salisbury Wilts, United Kingdom

[73] Assignee: The United States of America as represented by the Secretary of the Army, Washington, D.C.

[21] Appl. No.: 312,728

[22] Filed: Sep. 23, 1994

[51] Int. Cl.[6] ..... G01N 33/554; G01N 33/569

[52] U.S. Cl. ..... 435/7.32; 435/7.2; 435/7.5; 435/14; 435/18; 435/807

[58] Field of Search ..... 422/54, 68.1, 80, 422/82.01, 82.02, 83, 89, 90, 98; 435/7.2, 7.32, 7.5, 14, 18, 807; 436/528, 531, 153, 154, 155, 181, 806

*Primary Examiner*—Charles T. Jordan
*Assistant Examiner*—Meena Chelliah
*Attorney, Agent, or Firm*—John Callaghan

[57] ABSTRACT

A method and device for detecting bacteria by forming an immunoassay ladder using a biological substance (Ag) adsorbed onto a surface, to which has been added an immunological biochemical ladder (Ab) and beta-galactosidase enzyme (gal) to form a Ag-Ab-gal system. The system is added to an aqueous solution of an enzyme selected from ortho-nitrophenylgalactopyranoside and ortho-nitrophenylgalactosidase enzyme. The enzyme reacts with the gal to produce ortho-nitrophenol (ONP) such that the amount of ortho-nitrophenol (ONP) produced may be detected by measuring the vapor pressure generated by the ONP using an ion mobility spectrometer monitor. The pressure of the ONP is in proportion to the amount of biological substance present in the system. In a preferred embodiment, the ion mobility spectrometer monitor includes display means for indicating the quantity of bacteria measured. The surface on which the system is formed is preferably a plastic surface positioned in a cylindrical container sized to engage either an Airborne Vapor Monitor or a Chemical Agent Monitor, either of which may be hand held.

11 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CHEMICAL AGENT MONITOR FOR IMMUNOASSAY DETECTION

The invention described herein may be made, used, or licensed by or for the Government for Governmental purposes without the payment to me of any royalties thereon or therefor.

FIELD OF THE INVENTION

The present invention relates to the field detection of biological substances. More particularly the invention relates to the use of ion mobility spectroscopy in combination with immunoassay biochemical techniques to detect biological substances even in low concentrations and under field conditions rather than laboratory conditions of analysis.

BACKGROUND OF THE INVENTION

Truly portable, one-hand held-detectors of biological substances have not been commercially available. What has been available has been clinical kits that detect specific organisms. However, there is not presently any system that is capable of detecting organisms, protein toxins and biological substances in general, particularly if the system is to be used outdoors under less than totally tranquil circumstances.

It has been recently found to be possible to detect live, viable microorganisms by way of an inherent enzyme or enzymes. In this system live bacteria could be interrogated by their inherent enzymes that can be probed by certain compounds. Unfortunately for this system, only three enzymes can be probed; namely esterase, beta-galactosidase and glucosidase. The probe is limited because only three suitable compounds are commercially available and these are orthonitrophenylacetate, herein known as ONP acetate, ONP galactoside and ONP glucoside.

A number of techniques exist for the detection of bacteria in general. These techniques include the use of an excitation-emission matrix, 3-laser flowthrough cytometry, glucuronidase enzymes, aminopeptidase enzymes, extracellular enzymes and extracellular enzymes with nutrients. All of these techniques evoke a fluorescence response and require from 15 minutes to about four hours to achieve that response. Similarly, other techniques provide some of the sought after answers over a range of from 15 minutes, such as polarized light scattering to produce a Mueller matrix, to 9 hours where hydrogen and carbon dioxide are evolved over about 9 hours. Yet other techniques include gas chromatography to provide an ethanol metabolite, radiometry to produce $CO_2$, electrochemical techniques generating a hydrogen metabolite, simple organism growth to produce electrical impedance, and a light-addressable potentiometric sensor to provide a redox potential response. Also, enzyme linked lectinosorbent assay provides a lectin-conjugate, and extracellular enzymes provide a colorimetric response.

None of these techniques is effective over very short periods of time, measured in seconds from as low as one second up to a maximum of 90 seconds or thereabouts.

Another drawback for the above enumerated techniques is the inability to detect small or micro-small quantities of the desired bacteria and the like, in the order of 200 or 300 bacteria in a given period of time.

Also, most of the above described techniques are difficult or impossible to use in the field and under outdoor conditions that do not permit tranquil operation of the device.

Devices that depend upon complicated equipment do not survive in the field while comparative methods such as colorimetric methods and spectrophotometric measurements are not practical or even useful in some environments.

Accordingly it is an object of this invention to provide a method for detecting bacteria in general in a relatively short period of time of no more than about 90 seconds.

Another object of the present invention is to provide a system that can detect low levels of bacteria in short periods of time.

Yet another object of the present invention is to provide a method for detecting bacteria using a technique that employs vapor pressure rather than colorimetric or spectrophotometric measurements.

Other Objects will appear hereinafter.

SUMMARY OF THE INVENTION

It has now been discovered that the above and other objects of the present invention may be accomplished in the following manner. Specifically, a method and device for detecting bacteria have been discovered which accomplish the foregoing objectives.

The invention comprises forming an immunoassay ladder using a biological substance or antigen (Ag) adsorbed onto a surface, to which has been added an immunological biochemical antibody (Ab) and beta-galactosidase enzyme (gal) to form a Ag-Ab-gal system. The system is added to an aqueous solution of a reactant that reacts with the system in proportion to the amount of biological substance present. The reactant is selected from ortho-nitrophenylgalactopyranoside and ortho-nitrophenylgalactoside.

The enzyme reacts directly with the gal that is attached to the system to produce ortho-nitrophenol (ONP). The amount of (ONP) produced is proportional to the amount of the ladder in the system, and that amount is directly proportional to the amount of Ag or biological substance present. Without the Ag, the Ab will not attach to the surface and will not be present for the gal to react.

The gal that is present due to the ladder being formed is then detected by measuring the vapor pressure generated by the ONP using an ion mobility spectrometer monitor. The pressure of the ONP is , as described, in direct proportion to the amount of biological substance present in the system.

The invention employs the concept that an antigen or Ag will bond with an antibody Ab and will then attach to the enzyme which in turn reacts to produce ortho-nitrophenol in proportion to the amount of antigen present, such that the proportional amount is represented by the vapor pressure of the ortho-nitrophenol or ONP. The antibody functions as a biochemical bullet that targets the specific biological sample.

In a preferred embodiment, the ion mobility spectrometer monitor includes display means for indicating the quantity of bacteria measured. The surface on which the system is formed is preferably a plastic surface positioned in a cylindrical container sized to engage the ion mobility spectrometer monitor.

BRIEF DESCRIPTION OF THE DRAWINGS

For a more complete understanding of the invention, reference is hereby made to the drawings, in which.

DETAILED DESCRIPTION OF THE PREFERRED EMBODIMENT

The present invention has its roots in the specific reaction of either ortho-nitrophenylgalactopyranoside or the related ortho-nitrophenylgalactoside (both referred to as ONPG) with the beta-galactosidase enzyme on the Ag-Ab-gal ladder. This reaction takes place only if an Ag was originally present to accept the Ab immunological ladder. The ONPG that is present reacts with the enzyme to form ONP, which is an intense yellow compound. The standard method of detection of ONP has been the use of a spectrophotometric analyzer (UV-VIS absorbance spectrophotometer) which measures the generation of the yellow intensity of the ONP over time in a standard quartz cuvette cell.

In the present invention, the vapor pressure of the ONP is measured using an ion mobility spectrometer monitor. Preferred are either an Airborne Vapor Monitor AVM or a Chemical Agent Monitor CAM, either of which may be hand held. Both the AVM and the CAM are commercially available ion mobility spectrometer monitors. One commercially available AVM is manufactured and sold by Graseby Dynamics Limited under the trade name Atmospheric Vapor Monitor. A commercially available CAM is manufactured and sold by Graseby Dynamics Limited under the trade name Chemical Agent Monitor.

What is unique about the present invention is that the method and device of this invention take advantage of the relatively high vapor pressure that ONP has. ONP is a yellow solid and it has a fairly high vapor pressure. Thus a vapor monitor, as opposed to a spectrophotometric or colorimetric unit may be used to detect the ONP. The CAM or AVM or the like described above is contacted with the resulting ONP from the reaction between the gal enzyme and the ONPG.

The principle of operation is as follows. The antigen or biological substance of interest is adsorbed on the plastic surface. In step two, a monoclonal antibody with specificity for the antigen is added, followed by a biotinylated goat anti-mouse and amplified with β-galactosidase, labeled streptavidin, to form an immunological ladder. Next the enzyme substrate ONPG is added to the plastic surface and immediately the plastic surface is placed in a small cylindrical container. The container is inserted into the from end of the CAM or AVM. The ONPG is cleaved into two products by the enzyme. One of the products is vaporous, that being of course the ONP. Within seconds to at most one or two minutes the ONP is observed by the CAM. The CAM, or AVM as desired, employs ion mobility spectrometry and operates at atmospheric pressure. The compound is ionized and its time- of-flight is measured to determine the ion specie. An electrical gradient from negative to positive is utilized to produce output signals based upon time of travel. Small ions travel faster than large ions in the electrical gradient.

Figure 1:
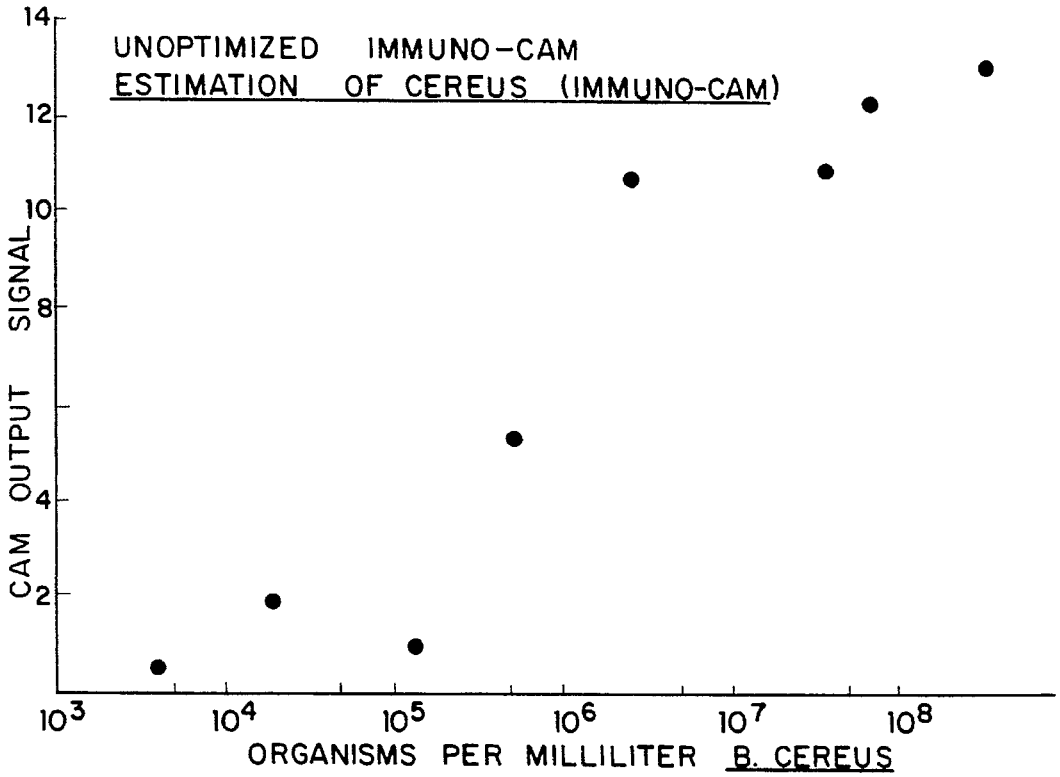
FIG. 1 is a sigmoid response curve of a CAM signal versus bulk *B. cereus* organism concentration using the method and device of the present invention.

In order to evaluate the efficiencies of the present invention, a sigmoid response curve of a CAM signal versus bulk *B. cereus* organism concentration was generated using the method and device of the present invention. Specifically concentration of bacteria in bulk stock organism suspensions of a few milliliters were tested. A plastic surface was immersed in the stock solution to allow some of the bacteria to adsorb on the surface. It is expected that less than 1% of the organisms in the bulk suspension would be adsorbed on the surface. Results are shown in FIG. 1, where the curve was obtained. For comparison purposes, FIG. 2 illustrates a similar curve except that the data was obtained with a standard Enzyme-Linked Immunosorbent Assay technique.

Figure 2:
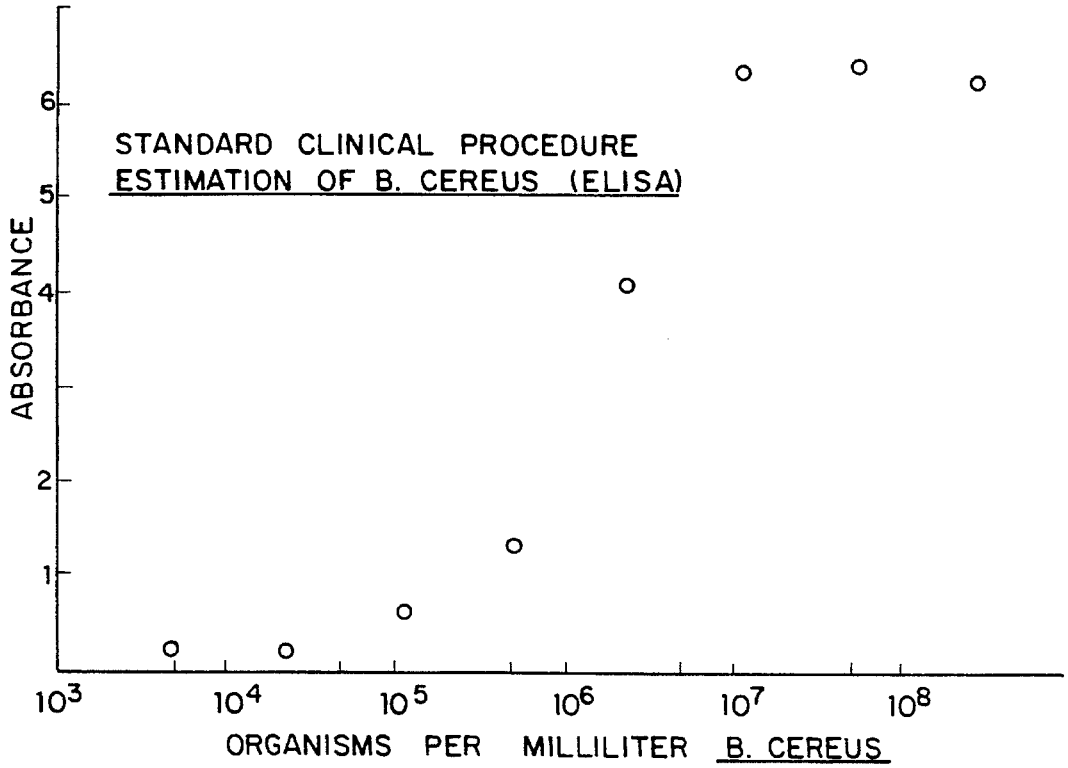
FIG. 2 is a similar curve except that the data were obtained with a standard Enzyme-Linked Immunosorbent Assay technique.

It is noted that one can place FIG. 1 over FIG. 2 to verify that similar curves have been observed and produced. The CAM curve of the invention, shown in FIG. 1, illustrates an almost ten-fold improvement in sensitivity at the lower concentration end, of a 10,000 bulk organism suspension versus a 100,000 organism bulk suspension. Both figures show the concentration of bulk stock organism suspensions of merely a few milliliters. It is seen that the CAM curve suggests that detection of approximately 200–300 *Bacillus cereus* can be obtained in a minutes time frame, a result not heretofore attainable.

The present invention is admirably suited for use with a wide variety of bacteria. Sigmoid-shaped curves similar to FIG. 1 were obtained with a variety of biological compounds such as the actual lipopolysaccharide endotoxin (cell surface protein markers) of influenza and pneumonia bacteria.

While particular embodiments of the present invention have been illustrated and described herein, it is not intended that these illustrations and descriptions limit the invention. Changes and modifications may be made herein without departing from the scope and spirit of the following claims.

We claim:

1. A method of detecting bacteria, comprising the steps of:

forming an immunoassay ladder including a biological substance (Ag) adsorbed onto a surface, adding an immunological biochemical ladder (Ab) and beta-galactosidase enzyme (gal) to form a Ag-Ab-gal system;

adding said system to an aqueous solution of an enzyme selected from ortho-nitrophenylgalactopyranoside and ortho-nitrophenylgalactosidase enzyme; and detecting the amount of ortho-nitrophenol (ONP) produced by measuring the vapor pressure generated by said ONP using an ion mobility spectrometer monitor, said pressure being in proportion to the amount of biological substance present in said system.

2. The method of claim 1, wherein said ion mobility spectrometer monitor includes display means for indicating the quantity of bacteria measured.

3. The method of claim 2, wherein said surface is a plastic surface positioned in a cylindrical container sized to engage an Airborne Vapor Monitor.

4. The method of claim 3, wherein said Airborne Vapor Monitor is hand held.

5. The method of claim 2, wherein said surface is a plastic surface positioned in a cylindrical container sized to engage a Chemical Agent Monitor.

6. The method of claim 5, wherein said Chemical Agent monitor is hand held.

7. A device for detecting bacteria, comprising:

a container attached to an ion mobility spectrometer monitor, said container having a surface therein having been contacted with an immunoassay ladder of a biological substance (Ag) adsorbed onto said surface, with an immunological biochemical ladder (Ab) and beta-galactosidase enzyme (gal), to form a Ag-Ab-gal system;

an aqueous solution added to said system comprising a solution of at least one enzyme selected from ortho-nitrophenylgalactopyranoside and ortho-nitrophenylgalactosidase; and indicator means on said monitor for displaying the amount of ortho-nitrophenol (ONP) produced in said solution by measuring the vapor pressure generated by said ONP, said pressure being in proportion to the amount of biological substance present in said system.

8. The device of claim 7, wherein said surface is a plastic surface positioned in a cylindrical container sized to engage an Airborne Vapor Monitor.

9. The device of claim 8, wherein said Airborne Vapor Monitor is hand held.

10. The device of claim 7, wherein said surface is a plastic surface positioned in a cylindrical container sized to engage a Chemical Agent Monitor.

11. The device of claim 10, wherein said Chemical Agent monitor is hand held.

* * * * *